United States Patent
Snell

(10) Patent No.: US 6,405,087 B1
(45) Date of Patent: Jun. 11, 2002

(54) CARDIAC STIMULATION SYSTEM PROVIDING IMPLANTABLE DEVICE PERFORMANCE EVALUATION AND METHOD

(75) Inventor: Jeffery D. Snell, Oak Park, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 09/513,886

(22) Filed: Feb. 25, 2000

(51) Int. Cl.[7] .............................................. A61N 1/37
(52) U.S. Cl. ........................................ 607/27; 607/28
(58) Field of Search ..................................... 607/27, 28

(56) References Cited

U.S. PATENT DOCUMENTS

| | | | |
|---|---|---|---|
| 4,295,474 A | 10/1981 | Fischell | 128/697 |
| 4,399,821 A | 8/1983 | Bowers | 128/630 |
| 4,566,464 A | 1/1986 | Piccone et al. | 128/732 |
| 4,809,697 A | 3/1989 | Causey, III et al. | 128/419 PT |
| 4,825,869 A | 5/1989 | Sasmor et al. | 128/419 |
| 4,865,044 A | 9/1989 | Wallace et al. | 128/736 |
| 4,871,351 A | 10/1989 | Feingold | 604/66 |
| 4,944,299 A | 7/1990 | Silvian | 128/419 PG |
| 4,981,139 A | 1/1991 | Pfohl | 128/671 |
| 5,076,272 A | 12/1991 | Ferek-Petric | 128/419 PG |
| 5,113,869 A | 5/1992 | Nappholz et al. | 128/696 |
| 5,360,437 A | 11/1994 | Thompson | 607/30 |
| 5,383,909 A | 1/1995 | Keimel | 607/7 |
| 5,404,877 A | 4/1995 | Nolan et al. | 128/671 |
| 5,417,717 A | 5/1995 | Salo et al. | 607/18 |
| 5,466,254 A | 11/1995 | Helland | 607/123 |
| 5,549,654 A | 8/1996 | Powell | 607/32 |
| 5,660,183 A | 8/1997 | Chiang et al. | 128/695 R |
| 5,693,076 A | 12/1997 | Kaemmerer | 607/59 |
| 5,722,999 A | 3/1998 | Snell | 607/32 |
| 6,129,746 A | * 10/2000 | Levine et al. | 607/27 |
| 6,233,487 B1 | * 5/2001 | Mika et al. | 607/27 |
| 6,285,908 B1 | * 9/2001 | Mann et al. | 607/28 |
| 6,317,633 B1 | * 11/2001 | Jorgenson et al. | 607/28 |

* cited by examiner

Primary Examiner—Carl Layno

(57) ABSTRACT

An implantable cardiac stimulation system and method wherein the implanting physician may store, in the system, parameters which define the expected performance of the device in conjunction with the programming of the device to address the needs of the patient. The person performing follow-up testing of the device and its interaction with the patient may, with an external programmer, be advised of the expected performance of the device at follow-up. The implanted device generates performance data indicative of the interaction between the device and the patient's heart. Limits, defining the expected interaction of the device and the patient's heart associated with the generated data are established and stored, either in the implantable device or in the external programmer. After implant, the generated data is evaluated to determine if the generated data satisfies the established limits. The evaluation results are then reported.

55 Claims, 2 Drawing Sheets

CARDIAC STIMULATION SYSTEM PROVIDING IMPLANTABLE DEVICE PERFORMANCE EVALUATION AND METHOD

FIELD OF THE INVENTION

The present invention generally relates to a cardiac stimulation system. The invention more particularly relates to such a system which includes and provides performance evaluation of an implantable cardiac stimulation device for determining if the implanted device is performing as expected.

BACKGROUND OF THE INVENTION

Implantable cardiac stimulation devices are well known in the art. They include implantable pacemakers which provide stimulation pulses to a heart to cause a heart, which would normally or otherwise beat too slowly or at an irregular rate, to beat at a controlled normal rate. They also include defibrillators which detect when the atria and/or the ventricles of the heart are in fibrillation and apply cardioverting or defibrillating electrical energy to the heart to restore the heart to a normal rhythm. Implantable cardiac stimulation devices may also include the combined functionalities of a pacemaker and a defibrillator.

As is well known, implantable cardiac stimulation devices sense cardiac activity for monitoring the cardiac condition of the patient in which the device is implanted. By sensing the cardiac activity of the patient, the device is able to provide cardiac stimulation therapy when it is required.

When an implantable cardiac stimulation device is implanted in a patient, it is typically implanted to correct a symptom or problem which the patient is experiencing. Modern implantable devices include a telemetry circuit to permit them to be programmed by external devices, such as programmers, to best fit the needs of the patient. The device is thereafter checked periodically to ensure that the device is interacting with the patient's heart as intended and, hence, is performing as intended. If the device is not performing as intended or needed, its operation is then adjusted through programming to adjust the programmable parameters of the device.

The medical personnel performing the follow-up check is commonly not the same person who prescribed, implanted and initially programmed the device. Hence, the person performing the follow-up check may not be fully aware of the intended device performance for that patient. Further, even if the same person performs the follow-up check, that person may not recall the intended device performance details for that patient. As a result, the person responsible for the follow-up check will not know what the intended device performance is and, hence, if the device is performing as intended.

The follow-up process traditionally requires the making of judgements based upon observations of several characteristics of the patient with the implanted device. For example, this may include the taking of telemetered ECG recordings, programmed settings (i.e., mode, rate, refractory period, pulse amplitudes and pulse width, etc.), measured data (i.e., battery voltage, current and impedance, lead impedances, etc.) and performance data recorded by the device over at last prior recording period (i.e., patient paced and sensed, heart rate histograms, sensor rate histograms, etc.) which indicate the interaction of the patient with the implanted device. In addition, some implantable devices may provide telemetered notes made by the physician about the disease diagnosis for the patient, the purpose for the device implant and device component types and implant locations.

Even with the above mentioned wealth of information which may be provided to the follow-up medical personnel by modern day implantable cardiac devices, there still remains the problem of knowing what the intended device performance is and hence if the device is performing as intended for the patient. This problem will only become more difficult as future implantable devices provide even more programmability and types and quantity of diagnostic data.

SUMMARY OF THE INVENTION

The present invention provides an implantable cardiac stimulation system and method wherein the implanting physician may store, in the system, parameters which define the expected performance of the device in conjunction with the programming of the device to address the needs of the patient. The person performing follow-up testing of the device and its interaction with the patient may, with an external programmer, be advised of the expected performance of the device at follow-up.

In accordance with the present invention, the implanted device generates performance data indicative of the interaction between the device and the patient's heart, e.g., paced and sensed heart rate histograms, sensor rate histograms, etc. Performance limits, defining the expected interaction of the device and the patient's heart associated with the generated performance data are established and stored, either in the implantable device or in the external programmer. After implant, the generated performance data is evaluated to determine if the generated data satisfies the established performance limits and the evaluation results are reported.

In accordance with the present invention, the generated performance data may be stored in histogram format and the limits may be expressed as percents or ratios. The data and limits may relate to heart rate, rhythms, sensor rates, etc.

The limits may be stored either in the implantable device or an external device, such as a programmer. Similarly, the data evaluation may be performed by either the implantable device or the external device.

The reporting of the evaluation results may include reporting out of limit conditions, within limit conditions, the limits, and/or the generated data.

In accordance with a further aspect of the present invention, when the evaluation reveals that the generated data satisfies the established limits, the limits may be revised to facilitate future follow-up. The limit revisions may be based upon the generated data. Preferably, the generated data is used to establish a baseline and the limits are revised based upon the baseline.

The implantable device and the external device preferably include telemetry circuitry to facilitate interaction between the implanted device and the external device. The telemetry may be utilized for conveying the generated data, the limits and/or the evaluation results to the external device for analysis and/or display.

BRIEF DESCRIPTION OF THE DRAWINGS

Further features and advantages of the present invention may be more readily understood by reference to the following description taken in conjunction with the accompanying drawings, in which.

DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
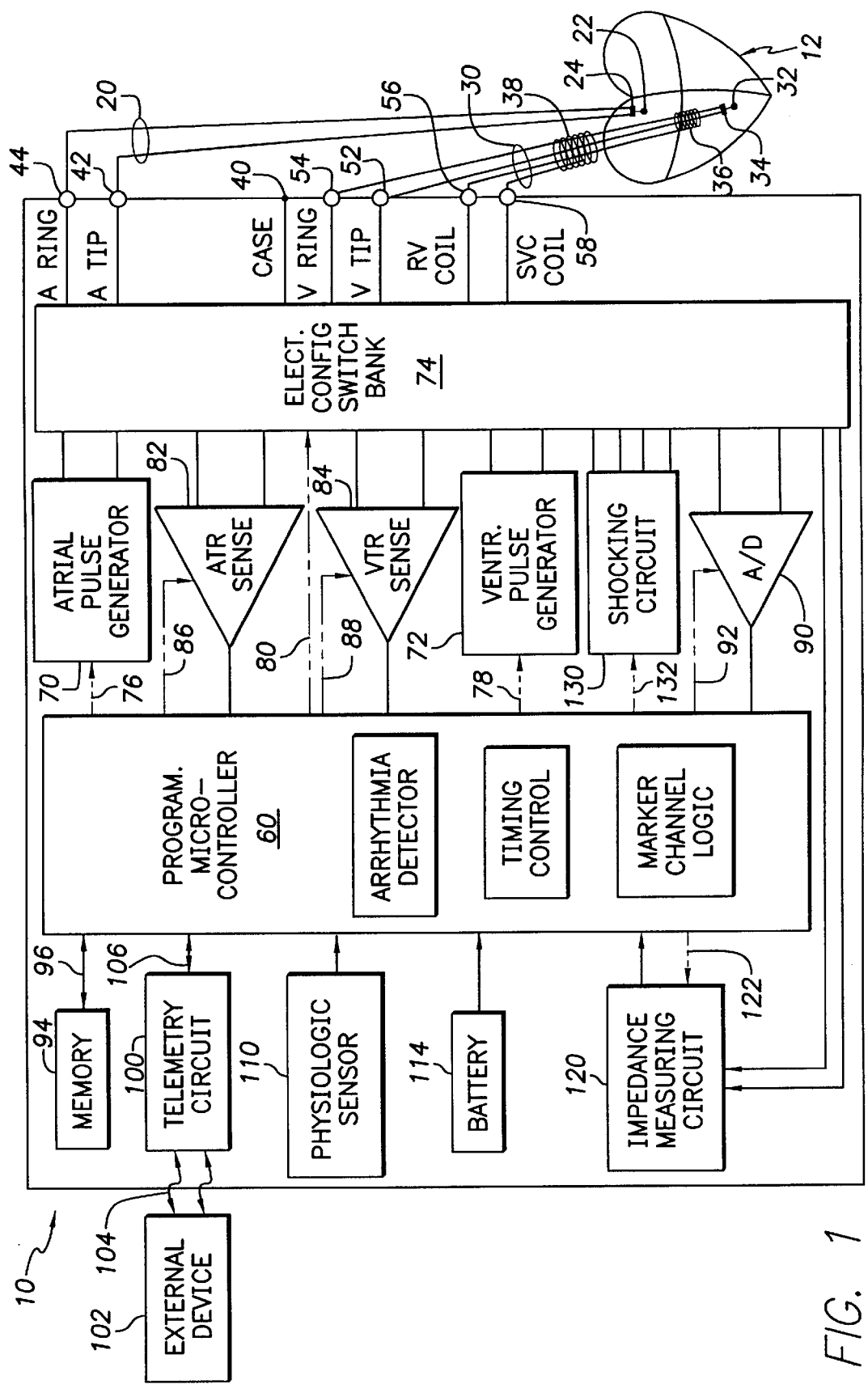
FIG. 1 is a functional block diagram of a dual-chamber implantable stimulation device illustrating the basic elements of a stimulation device which can provide cardioversion, defibrillation and pacing stimulation.

In FIG. 1, a simplified block diagram is shown of a dual-chamber implantable stimulation device 10 which is capable of treating both fast and slow arrhythmias with stimulation therapy, including cardioversion, defibrillation, and pacing stimulation. While a dual-chamber device is shown, this is for illustration purposes only, one of skill in the art could readily eliminate or disable the appropriate circuitry to provide a single-chamber stimulation device capable of treating one chamber with cardioversion, defibrillation and pacing stimulation or appropriate circuitry may be added to provide a three or four chamber stimulation device.

To provide atrial chamber pacing stimulation and sensing, the stimulation device 10 is shown in electrical communication with a patient's heart 12 by way of an implantable atrial lead 20 having an atrial tip electrode 22 and an atrial ring electrode 24 which typically is implanted in the patient's atrial appendage.

The stimulation device 10 is also shown in electrical communication with the patient's heart 12 by way of an implantable ventricular lead 30 having, in this embodiment, a ventricular tip electrode 32, a ventricular ring electrode 34, a right ventricular (RV) coil electrode 36, and an SVC coil electrode 38. Typically, the ventricular lead 30 is transvenously inserted into the heart 12 so as to place the RV coil electrode 36 in the right ventricular apex, and the SVC coil electrode 38 in the superior vena cava. Accordingly, the ventricular lead 30 is capable of receiving cardiac signals and delivering stimulation in the form of pacing and shock therapy to the right ventricle.

While only two leads are shown in FIG. 1, it is to be understood that additional stimulation leads (with one or more pacing, sensing and/or shocking electrodes) may be used in order to efficiently and effectively provide pacing stimulation to the side of the heart or atrial cardioversion and/or defibrillation. For example, a lead designed for placement in the coronary sinus region could be implanted to deliver left atrial pacing, atrial shocking therapy, and/or for left ventricular pacing stimulation. For a complete description of a coronary sinus lead, see U.S. patent application Ser. No. 09/196,898, "A Self-Anchoring Coronary Sinus Lead" (Pianca et al.); and U.S. Pat. No. 5,466,254, "Coronary Sinus Lead with Atrial Sensing Capability" (Helland), which patents are hereby incorporated herein by reference.

The housing 40 (shown schematically) for the stimulation device 10 includes a connector (not shown) having an atrial tip terminal 42 and an atrial ring terminal 44, which are adapted for connection to the atrial tip electrode 22 and the atrial ring electrode 24, respectively. The housing 40 further includes a ventricular tip terminal 52, a ventricular ring terminal 54, a right ventricular (RV) shocking terminal 56, and an SVC shocking terminal 58, which are adapted for connection to the ventricular tip electrode 32, the ventricular ring electrode 34, the RV coil electrode 36, and the SVC coil electrode 38, respectively. The housing 40 (often referred to as the "can", "case" or "case electrode") may be programmably selected to act as the return electrode, or anode alone or in combination with one of the coil electrodes, 36 and 38. For convenience, the names of the electrodes are shown next to the terminals.

At the core of the stimulation device 10 is a programmable microcontroller 60 or other processor which controls the various modes of stimulation therapy. As is well known in the art, the microcontroller 60 includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions is well known in the art.

As shown in FIG. 1, an atrial pulse generator 70 and a ventricular pulse generator 72 generate pacing stimulation pulses for delivery by the atrial lead 20 and the ventricular lead 30, respectively, via a switch bank 74. The pulse generators, 70 and 72, are controlled by the microcontroller 60 via appropriate control signals, 76 and 78, respectively, to trigger or inhibit the stimulation pulses. The microcontroller 60 further includes timing circuitry that controls the stimulation device's timing of such stimulation pulses.

The switch bank 74 includes a plurality of switches for switchably connecting the desired electrodes to the appropriate I/O circuits, thereby providing complete electrode programmability. Accordingly, the switch bank 74, in response to a control signal 80 from the microcontroller 60, determines the polarity of the stimulation pulses (e.g., unipolar or bipolar) by selectively closing the appropriate combination of switches (not shown) as is known in the art.

An atrial (ATR) sense amplifier 82 and a ventricular (VTR) sense amplifier 84 are also coupled to the atrial and ventricular leads 20 and 30, respectively, through the switch bank 74 for detecting the presence of cardiac activity. The switch bank 74 determines the "sensing polarity" of the cardiac signal by selectively closing the appropriate switches, as is also known in the art. In this way, the clinician may program the sensing polarity independent of the stimulation polarity.

Each sense amplifier, 82 and 84, preferably employs a low power, precision amplifier with programmable gain and/or automatic gain control, bandpass filtering, and a threshold detection circuit, known in the art, to selectively sense the cardiac signal of interest. The automatic gain control enables the device 10 to deal effectively with the problem of sensing the low frequency, low amplitude signal characteristics of ventricular fibrillation.

The outputs of the atrial and ventricular sense amplifiers, 82 and 84, are connected to the microcontroller 60 which, in turn, inhibit the atrial and ventricular pulse generators, 70 and 72, respectively, in a demand fashion whenever cardiac activity is sensed in the respective chambers. The sense amplifiers, 82 and 84, in turn, receive control signals over signal lines, 86 and 88, from the microcontroller 60 for purposes of controlling the gain, threshold, polarization charge removal circuitry (not shown), and the timing of any blocking circuitry (not shown) coupled to the inputs of the sense amplifiers, 82 and 86, as is known in the art.

For arrhythmia detection, the present invention utilizes the atrial and ventricular sense amplifiers, 82 and 84, to sense cardiac signals to determine whether a rhythm is physiologic or pathologic. As used herein "sensing" is reserved for the noting of an electrical depolarization, and "detection" is the processing of these sensed depolarization signals and noting the presence of an arrhythmia. The timing intervals between sensed events (e.g., the P-P and R-R intervals) are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks, also known as "tiered therapy").

Cardiac signals are also applied to the inputs of an analog to digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the atrial and ventricular leads, 20 and 30, through the switch bank 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy. In accordance with the present invention, a relatively large amount of data relating to the interaction of the device with the patient's heart may be stored in the memory 94, which data may then be used for subsequent analysis to determine if the device is performing as expected during a follow-up check.

Advantageously, the operating parameters of the implantable device 10 may be non-invasively programmed into the memory 94 through a telemetry circuit 100 in telemetric communication with an external device 102, such as a programmer. The telemetry circuit 100 is activated by the microcontroller by a control signal 106. The telemetry circuit 100 advantageously allows intracardiac electrograms and status information relating to the operation of the device 10 in addition to the data contained in the memory 94 relating to the interaction of the device with the patient's heart to be sent to the external device 102 through an established communication link 104. For examples of such devices, see U.S. Pat. No. 4,809,697, entitled "Interactive Programming and Diagnostic System for use with Implantable Pacemaker", (Causey, III et al.) and U.S. Pat. No. 4,944,299, entitled "High Speed Digital Telemetry System for Implantable Device" (Silvian).

In the preferred embodiment, the stimulation device 10 further includes a physiologic sensor 110. Such sensors are commonly called "rate-responsive" sensors. The physiological sensor 110 is used to detect the exercise state of the patient, to which the microcontroller 60 responds by adjusting the rate and AV delay at which the atrial and ventricular pulse generators, 70 and 72, generate stimulation pulses. A common type of rate responsive sensor is an activity sensor, such as an accelerometer or a piezoelectric crystal, which is mounted within the housing 40 of the stimulation device 10. Other types of physiologic sensors are also known, for example, sensors which sense the oxygen content of blood, respiration rate and/or minute ventilation, pH of blood, ventricular gradient, etc. However, any sensor may be used which is capable of sensing a physiological parameter which corresponds to the exercise state of the patient. The type of sensor used is not critical to the present invention and is shown only for completeness.

The stimulation device 10 additionally includes a battery 114 which provides operating power to all of the circuits shown in FIG. 1. For the stimulation device 10, which employs shocking therapy, the battery 114 must be capable of operating at low current drains for long periods of time, and then be capable of providing high-current pulses (for capacitor charging) when the patient requires a shock pulse. The battery 114 must also have a predictable discharge characteristic so that elective replacement time can be detected. Accordingly, the present invention preferably employs lithium/silver vanadium oxide batteries, as is presently true for many such devices.

The stimulation device 10 further includes a magnet detection circuitry (not shown) coupled to the microcontroller 60. It is the purpose of the magnet detection circuitry to detect when a magnet is placed over the stimulation device 10, which magnet may be used by a clinician or patient to perform various functions controlling the stimulation device 10.

As further shown in FIG. 1, the present invention preferably includes an impedance measuring circuit 120 which is enabled by the microcontroller 60 by a control signal 122. The known uses for an impedance measuring circuit 120 include, but are not limited to, lead impedance surveillance during the acute and chronic phases for proper lead positioning or dislodgment; detecting operable electrodes and automatically switching to an operable pair if dislodgment occurs; measuring respiration or minute ventilation; measuring thoracic impedance for determining shock thresholds; detecting when the device has been implanted; measuring stroke volume; and detecting the opening of the valves, etc. The impedance measuring circuit 120 is advantageously coupled to the switch bank 74 so that any desired electrode (including the RV and SVC coil electrodes, 36 and 38) may be used. The impedance measuring circuit 120 is not critical to the present invention and is shown for only completeness.

It is a further function of the device 10 to function as an implantable cardioverter/defibrillator (ICD) device. That is, it detects the occurrence of an arrhythmia, and automatically applies an appropriate electrical shock therapy to the heart aimed at terminating the detected arrhythmia. To this end, the microcontroller 60 further controls a shocking circuit 130 by way of a control signal 132. The shocking circuit 130 generates shocking pulses of low (up to 0.5 joules), moderate (0.5–10 joules), or high energy (11–40 joules), as controlled by the microcontroller 60. Such shocking pulses are applied to the patient's heart through at least two shocking electrodes as shown in this embodiment using the RV and SVC coil electrodes, 36 and 38, respectively. In alternative embodiments, the housing 40 may act as an active electrode in combination with the RV electrode 36 alone, or as part of a split electrical vector using the SVC coil electrode 38 (i.e., using the RV electrode as a common electrode).

Cardioversion shocks are generally considered to be of low to moderate energy level. Defibrillation shocks are generally of moderate to high energy level and pertain exclusively to the treatment of fibrillation. Accordingly, the microcontroller 60 is capable of controlling the delivery of the shocking pulses.

In accordance with the present invention, the device 10 and external device 102 provide combined functionality to assist medical personnel, after implant, in determining if the device is performing as expected. To that end, the microcontroller 60 generates performance data relating to the interaction of the device 10 with the patient's heart 12. The performance data is stored in the memory 94, preferably in histogram form, to permit a large amount of data to be accommodated over a relatively long term period between follow-up checks. The performance data generated by the processor 60 includes data indicative of the interaction of the device 10 and the patient's heart 12, for example, heart rate, heart rhythm, sensor indicated rate, percent paced, etc.

With respect to heart rate, the microcontroller 60 may generate a rate histogram by counting the amount of time where the heart beats fall in each of thirty-two (32) rate intervals from 30 ppm to 350 ppm. With respect to heart rhythm, the counting may be further segregated by pacing mode (AV, AR, PV, PR, or PVC) for dual chamber pacing, or paced and sensed for single chamber pacing.

With respect to sensor indicated rate, the microcontroller 60 may generate a sensor indicated rate histogram. It may do so by counting the amount of time where the sensor indicated rate of the sensor 110 falls into each of thirty-two (32) rate intervals from 30 ppm to 200 ppm.

With respect to percent paced, the microcontroller 60 may generate a percent paced histogram by counting the number of heart beats or time in which beats are paced versus intrinsic. The counting may be further segregated by atrial event pacing or sensing and ventricular event pacing or sensing for dual chamber pacing.

In order to determine if the implantable device 10 is performing as expected, limits associated with the generated performance data are established. The limits may be maintained either in the memory 94 of the device 10 after being telemetered to the device 10 from the external device 102, or the limits may be maintained in the external device 102 itself. The benefit of maintaining the limits within the device 10 is that any external device, compatible with the device 10 and capable of accessing the limits by telemetry along with data, could be utilized for evaluating data against the limits whereas maintaining the limits in the external device 102 requires that particular external device 102 to be used in performing the evaluation or transfer of the limits from that external device 102 to another external device to be used for the evaluation.

The established limits relating to the data may be simple thresholds based upon percentages or ratios. As an example, a set of typical established limits may be: (1) no more than five percent (5%) of all rate histogram counts should be above 120 ppm; (2) at least fifty percent (50%) of the rhythm histogram counts should be either PV or PR; (3) all lead impedance measurements in the atrium should fall between 380 and 680 ohms; (4) at least one percent (1%) of all sensor indicated rate histogram counts should be between 100 ppm and 150; and (5) at least sixty percent (60%) of all sensor indicated rate histogram counts should be below 80 ppm.

After the device is implanted, for example at the first follow-up check, the data is evaluated based upon the established limits. The evaluation could be performed by the microcontroller 60 of the device 10 or by the external device 102 after receiving the data and limits from the device by telemetry.

After the data is evaluated against the limits, the results of the evaluation are reported. To that end, the results may be displayed by a video display or printout, for example, by the external device 102. If the evaluation is performed by the microcontroller 60 of the device 10, the results are displayed by the external device 102 after receiving the same from the device 10 by telemetry. The displayed results include out of limit conditions and may additionally include the established limits and the data.

The evaluation results, if out of limit conditions, may be reported as alerts by using highlighted or contrasting display colors, arrows, or special borders or patterns. The expectations could be graded into two or more levels of concern. One level could be a simple notice while another level may be a warning and yet another level may generate an alarm. The report may further include the variations in which the diagnostic counters deviated from expectations.

Having the report information in hand, the medical personnel will be able to know if the device 10 is performing as expected and what the expectations were. If there are any out of limit conditions, the personnel will be advised of that fact and be able to modify the device programming towards achieving the expected performance.

If the evaluation reveals that the gathered data satisfies the established limits, the limits may then be revised based upon the data used in the evaluation. The limit revisions may be performed by the microcontroller 60 of the device 10 or by the external device 102 and then conveyed to the device 10 by telemetry. The revised limits may be determined by establishing a baseline from the generated data and deriving permitted deviations, such as plus and minus fifteen percent (15%), from the baseline for future follow-up checks. In this manner, future evaluation of device performance may be obtained.

Figure 2:
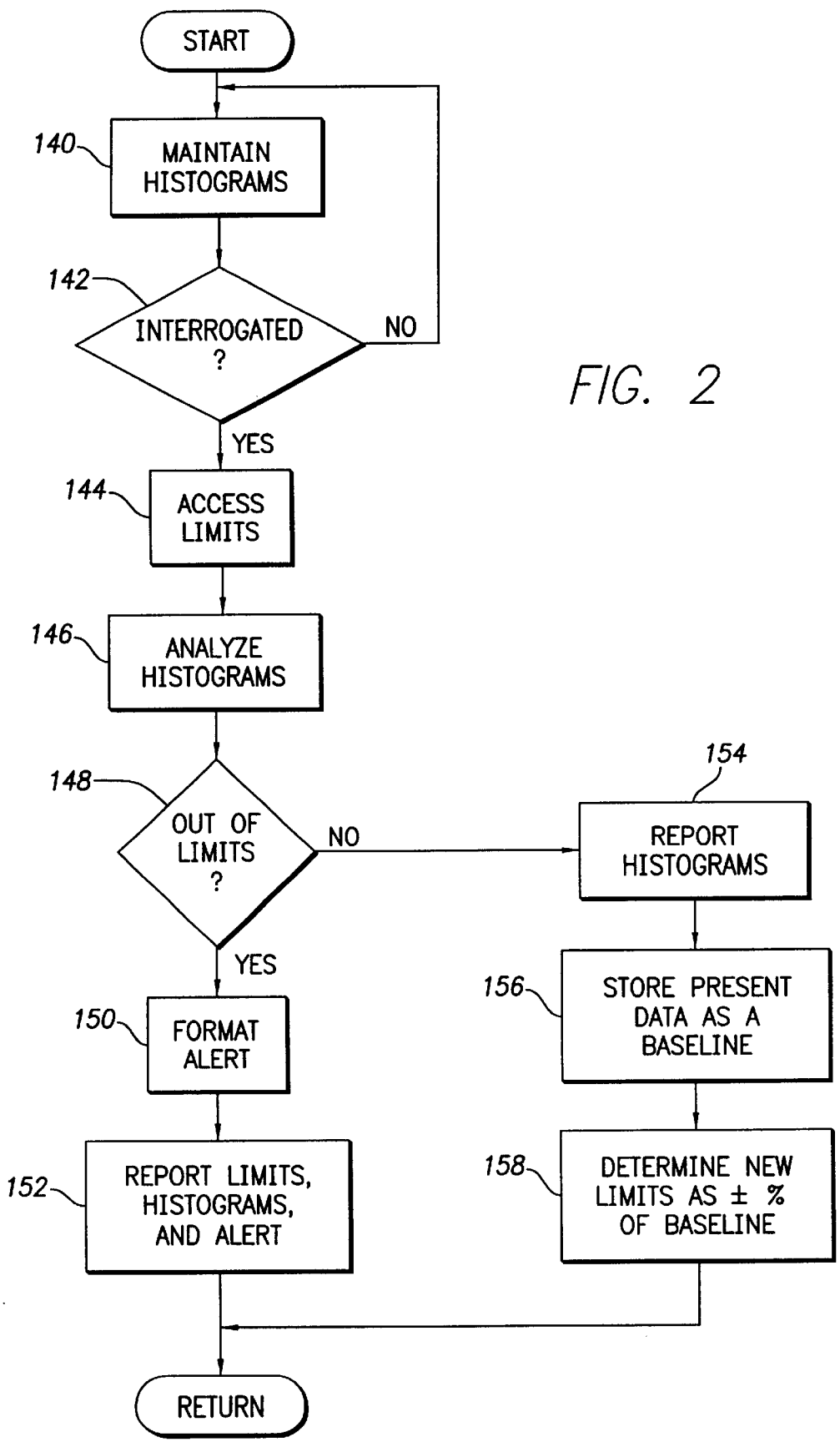
FIG. 2 is an exemplary flow chart describing an overview of the operation of the present invention.

In FIG. 2, an exemplary flow chart is shown describing an overview of the operation of the novel features of the present invention. In this flow chart, the various algorithmic steps are summarized in individual "blocks". Such blocks describe specific actions or decisions that must be made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

The process illustrated in FIG. 2 begins with activity block 140. In accordance with activity block 140, the histograms of the generated data are maintained and updated after the implantable device 10 is implanted in the patient, initially programmed, and the device performance limits are established. The process then proceeds to decision block 142 wherein the device 10 determines if it is being interrogated, as for example, at the first follow-up check. If the device 10 is not being interrogated, it returns to activity block 140 to continue to generate histogram data representing the interaction of the device with the patient's heart 12.

If the device 10 is being interrogated, as for example at the first follow-up check, the process advances to activity block 144 wherein the microcontroller 60 accesses the established limits relating to the generated data. Following activity block 144 the process continues to activity block 146 wherein the generated histogram data is evaluated against the limits accessed in activity block 144. If the activity block 144 is performed in the external device 102, and the limits are stored in the device 10, the limits and data, prior to activity block 146, are conveyed to the external device 102 for analysis.

Once the data is analyzed in accordance with activity block 146, the process proceeds to decision block 148 wherein it is determined if there are any out of limit conditions. Again, decision block 148 may be performed either in the device 10 by the microcontroller 60 or in the external device 102. If there is at least one out of limit condition as determined in decision block 148, the process proceeds to activity block 150 wherein an alert is formatted to report the out of limit condition or conditions. Again, activity block 150 may be performed by either microcontroller 60 of device 10 or the external device 102.

Once the alert is formatted, the process advances to activity block 152 where a report is displayed by the external device 102. If the microcontroller 60 formats the alert and performs the data analysis, the particulars to be reported, which may include the alert, the histogram data, the within limits conditions, and the limits, are first conveyed to the external device 102 by telemetry. The foregoing may then be displayed by the external device 102.

Having the reported information in hand, the medical personnel conducting the follow-up check will be advised as to the expected performance of the device 10 and those parameters in which the device is not performing as expected. The device 10 may then be reprogrammed towards complete satisfactory performance.

If in decision block 148 it is determined that the data satisfies the established limits (there are no out of limit conditions), the process advances to activity block 154 wherein the histogram data is displayed by the external device 102. The limits may also be displayed at this time.

Once the report is displayed in activity block 154, the process advances to activity block 156 wherein the generated histogram data is utilized to establish a baseline. Once the baseline is established, the process advances to activity block 158 wherein the baseline is used to establish revised limits. Each revised limit may be expressed as plus and minus X percent, such as plus and minus fifteen percent (15%), of the baseline for each limit parameter. The revised limits may thereafter be used for future follow-ups.

As will be appreciated by those skilled in the art, activity blocks 156 and 158 may be performed by either the microcontroller 60 of device 10 or by the external device 102. Following activity block 158, the process returns.

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What is claimed is:

1. A system for evaluating the interaction of an implantable cardiac stimulation device and a heart of a patient, the system comprising:

data generating means for generating performance data indicative of the interaction of the implantable cardiac stimulation device and the patient's heart;

limit means for establishing at least one performance limit associated with the generated performance data;

analyzing means for analyzing the performance data with respect to the at least one established limit to determine an out of limit condition; and reporting means for reporting the out of limit condition.

2. The system of claim 1 wherein the analyzing means includes means for determining out of limit conditions with respect to the established limits.

3. The system of claim 1 wherein the analyzing means includes means for determining within limit conditions with respect to the established limits.

4. The system of claim 1 wherein the reporting means includes telemetry means for transmitting the generated data, the established limits, and the results to an external device for display.

5. The system of claim 1 wherein:

the data generating means is within the implantable device; and wherein the implantable device includes telemetry means for transmitting the generated data to an external device for analysis.

6. The system of claim 1 wherein:

the data generating means and limit means are within the implantable device; and wherein the implanted device includes telemetry means for transmitting the generated data and established limits to an external device.

7. The system of claim 1 wherein:

the data generating means, the limit means and the analyzing means are within the implantable device; and wherein the implantable device includes telemetry means for transmitting the generated data, the established limits, and the results to an external device.

8. The system of claim 2 further including an external device including the reporting means for reporting the out of limit conditions.

9. The system of claim 2 further including limit revising means for revising the established limits responsive to the analyzing means failing to determine an out of limit condition.

10. The system of claim 2 further including limit revising means for revising the established limits responsive to the analyzing means failing to determine an out of limit condition, the limit revising means revising the established limits based upon data generated by the data generating means.

11. The system of claim 2 further including limit revising means, responsive to the analyzing means failing to determine an out of limit condition, for establishing a baseline based upon data generated by the data generating means and revised limits based upon the established baseline.

12. The system of claim 5 wherein the implantable cardiac stimulation device includes memory means for storing the generated data.

13. The system of claim 5 wherein the implantable cardiac stimulation device includes memory means for storing the generated data in histogram format.

14. A system for evaluating interaction between an implantable cardiac stimulation device and a patient's heart, the system comprising:

a processor, within the implantable device, programmed to generate performance data representing interaction between the device and the patient's heart;

an analyzer that determines if the generated performance data satisfies established performance limits; and an external device that reports the established limits and analyzer results.

15. The system of claim 14 wherein the analyzer determines out of limit conditions for generated data failing to satisfy the established limits.

16. The system of claim 14 wherein the analyzer is within the implantable device.

17. The system of claim 14 wherein the processor is programmed to provide the analyzer that determines if the generated data satisfies the established limits.

18. The system of claim 14 wherein the processor is further programmed to establish revised limits when the generated data satisfies the established limits.

19. The system of claim 14 wherein the processor is programmed to establish the revised limits based upon the generated data.

20. The system of claim 16 wherein the implantable device further includes a telemetry circuit that transmits the established limits and analyzer results to the external device.

21. The system of claim 14 wherein the analyzer is within the external device.

22. The system of claim 21 wherein the implantable device includes a telemetry circuit that transmits the generated data to the external device for analysis.

23. The system of claim 22 wherein the analyzer establishes revised limits when the generated data satisfies the established limits.

24. The system of claim 22 wherein the analyzer establishes the revised limits based upon the generated data.

25. The system of claim 14 wherein the implantable cardiac stimulation device includes a memory that stores the generated data.

26. The system of claim 25 wherein the processor is programmed to store the generated data in the memory in histogram format.

27. A method of evaluating the interaction of an implantable cardiac stimulation device and a heart, the method comprising the steps of:
    gathering performance data indicative of the interaction of the implantable cardiac stimulation device and the patient's heart;
    establishing performance criteria associated with the generated performance data;
    evaluating the data to determine if the performance data satisfies the criteria; and
    reporting the established criteria and evaluation results.

28. The method of claim 27 wherein the evaluation results are out of limit conditions.

29. The method of claim 27 wherein the evaluation results are within limit conditions.

30. The method of claim 27 wherein:
    the data gathering step is performed within the implantable device; and wherein
    the method further includes the step of conveying the gathered data from the implantable device to an external device for evaluation.

31. The method of claim 30 wherein:
    the establishing step is performed within the implantable device; and wherein
    the method further includes the step of conveying the established criteria with the gathered data from the implantable device to the external device for evaluation.

32. The method of claim 31 wherein:
    the evaluating step is performed within the implantable device; and wherein
    the method further includes the step of conveying the gathered data, the established criteria, and the evaluation results from the implantable device to the external device.

33. The method of claim 27 further including the step of revising the established criteria when the gathered data satisfies the established criteria.

34. The method of claim 27 further including the step of revising the established criteria, based upon the gathered data, when the gathered data satisfies the established criteria.

35. The method of claim 34 wherein the revising step includes the steps of establishing a baseline based upon the gathered data and setting revised limits based upon the established baseline.

36. The method of claim 27 wherein the data gathering step includes the step of storing the gathered data in a memory prior to the evaluating step.

37. The method of claim 36 wherein the data gathering step further includes storing the data in histogram format.

38. An external system for evaluating performance of an implantable cardiac stimulation device with a patient's heart, the external system comprising:
    means for programming a plurality of parameters in the stimulation device to address the needs of the patient;
    means for defining criteria for an expected performance based on the programmed plurality of parameters;
    means for receiving performance data from the stimulation device indicative of the actual interaction of the stimulation device and the patient's heart over an extended period of time; and
    means for reporting the received performance data with the expected performance criteria.

39. The external system of claim 38, wherein the reporting means comprises means for reporting the performance data in the form of histogram data.

40. The external system of claim 39, wherein the performance data in the form of histogram data comprises rate histogram data defined as the amount of time that the heart rate falls in predetermined rate bins.

41. The external system of claim 39, wherein the performance data in the form of histogram data comprises a histogram of a paced and sensed events.

42. The external system of claim 39, wherein the performance data in the form of histogram data comprises rhythm histogram data defined as the amount of time that the heart rate remains in AV, AR, PV and PR pacing modes.

43. The external system of claim 39, wherein the performance data in the form of histogram data comprises sensor indicated rate histogram data defined as the amount of time that the sensor indicated rate falls in predetermined rate bins.

44. The external system of claim 38, further comprising means for displaying alerts using at least one of display colors, arrows, special borders, patterns, numerical values, percentages, and ratios.

45. The external system of claim 38, further comprising means for displaying alerts according to a level of concern.

46. The external system of claim 38, further comprising means for displaying a first level of alert corresponding to a simple notice.

47. The external system of claim 46, further comprising means for displaying a second level of alert corresponding to a warning.

48. The external system of claim 47, further comprising means for displaying a third level of alert corresponding to an alarm condition.

49. A system for evaluating an expected performance of an implantable cardiac stimulation device, the system comprising:

an implantable device, comprising:

control circuitry that programmably alters a plurality of parameters to address the needs of the patient;

a memory circuit that stores performance data indicative of the actual performance of the device based on the plurality of programmed parameters, and stores an expected performance criteria based on the plurality of programmed parameters; and a telemetry circuit that transmits the actual performance data with the expected performance criteria;

an external device, comprising:

a telemetry circuit that receives the actual performance data with the expected performance criteria; and a display device that displays the actual performance data with the expected performance.

50. The external system of claim 49, wherein the memory circuit stores performance data over an extended period of time.

51. The external system of claim 50, wherein the memory circuit compresses the performance data.

52. The external system of claim 51, wherein the compressed performance data comprises histogram data.

53. The external system of claim 52, wherein the histogram data comprises at least one of rate, rhythm, sensor indicated rate histogram data, paced event, and sensed event histogram data.

54. The external system of claim 49, further comprising means for displaying alerts using at least one of display colors, arrows, special borders, patterns, numerical values, percentages, and ratios.

55. The external system of claim 49, further comprising means for displaying alerts according to at least one of a simple notice, a warning, and an alarm condition.

* * * * *